United States Patent
Batman et al.

(10) Patent No.: US 8,895,315 B2
(45) Date of Patent: *Nov. 25, 2014

(54) DISPLAYING STATUS OF A BLOOD GLUCOSE MEASURE BEING TRANSFERRED WIRELESSLY FROM A HANDHELD GLUCOSE METER

(71) Applicant: Roche Diagnostics Operations, Inc., Indianapolis, IN (US)

(72) Inventors: Carol J. Batman, Indianapolis, IN (US); Stacia Davis, McCordsville, IN (US); David B. Markisohn, Indianapolis, IN (US); Erin K. McKinney, Brownsburg, IN (US); Mark G. Mears, Westfield, IN (US); Amy S. Stanley, Noblesville, IN (US); Benjamin E. Strickrod, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1 day.

This patent is subject to a terminal disclaimer.

(21) Appl. No.: 13/794,919

(22) Filed: Mar. 12, 2013

(65) Prior Publication Data
US 2014/0273256 A1 Sep. 18, 2014

(51) Int. Cl.
*G01N 33/66* (2006.01)
*G01N 33/48* (2006.01)
*G08C 17/02* (2006.01)

(52) U.S. Cl.
CPC ............... *G08C 17/02* (2013.01); *G01N 33/66* (2013.01); *Y10S 128/903* (2013.01); *Y10S 128/904* (2013.01)
USPC ............. 436/95; 436/63; 435/14; 700/266; 128/903; 128/904

(58) Field of Classification Search
CPC ............. A61B 5/0002; A61B 5/14532; A61B 2560/0271; A61B 2562/0295; G06F 19/3418; G06F 19/3487; G01N 33/48; G01N 33/49; G01N 33/66; G01N 2800/042
USPC ......... 436/63, 95; 435/14; 600/300, 347, 365; 700/266; 128/903, 920, 904
See application file for complete search history.

(56) References Cited

U.S. PATENT DOCUMENTS

| | | | |
|---|---|---|---|
| 5,491,784 A | 2/1996 | Douglas et al. | |
| 8,066,639 B2* | 11/2011 | Nelson et al. | 600/301 |
| 8,335,569 B2 | 12/2012 | Aghassian | |
| 2006/0036134 A1 | 2/2006 | Tarassenko et al. | |
| 2008/0177154 A1* | 7/2008 | Hansen et al. | 600/300 |
| 2008/0194934 A1* | 8/2008 | Ray et al. | 600/347 |
| 2010/0228111 A1* | 9/2010 | Friman et al. | 600/365 |
| 2010/0305421 A1* | 12/2010 | Ow-Wing | 600/365 |
| 2010/0331645 A1 | 12/2010 | Simpson et al. | |
| 2011/0124996 A1 | 5/2011 | Reinke et al. | |
| 2014/0051958 A1* | 2/2014 | Fern et al. | 600/365 |

\* cited by examiner

*Primary Examiner* — Maureen Wallenhorst
(74) *Attorney, Agent, or Firm* — Harness, Dickey & Pierce, P.L.C.

(57) ABSTRACT

Persons with diabetes often carry a handheld glucose meter as well as a portable computing device, such as a mobile phone. Given the close proximity of these two devices, the portable computing device can serve as a data collector for the glucose measures taken by the glucose meter. Improved techniques are set forth for transferring glucose measures automatically and seamlessly to the patient's portable computing device, including displaying a value for the glucose measure along with an identifier for the portable computing device on a display of the glucose meter during the data exchange with the portable computing device.

13 Claims, 7 Drawing Sheets

DISPLAYING STATUS OF A BLOOD GLUCOSE MEASURE BEING TRANSFERRED WIRELESSLY FROM A HANDHELD GLUCOSE METER

FIELD

The present disclosure relates to techniques for transferring data from a handheld glucose meter automatically to a portable communication device.

BACKGROUND

Persons with diabetes have difficulty regulating blood glucose levels in their bodies. As a consequence, many of these persons carry specialized electronic meters, called blood glucose meters, which allow them to periodically measure their glucose levels and take appropriate action, such as administering insulin. These persons may also carry with them a portable communication device, such as a mobile phone, a personal digital assistant, a tablet or similar device. People often rely on their portable communication device as the primary means for planning, scheduling and communicating with others. As a result, most portable communication devices are equipped with sophisticated software which provides user-friendly means for viewing and inputting data. Accordingly, a person with diabetes may wish to wirelessly transmit the results of a blood glucose measurement from their glucose meter to their portable communication device in order, for example, to display, analyze or report on the data.

Therefore, it is desirable to develop improved techniques for transferring blood glucose measures from a glucose meter automatically via a wireless data link to a diabetes management application residing on a portable communication device.

This section provides background information related to the present disclosure which is not necessarily prior art.

SUMMARY

Persons with diabetes often carry a handheld glucose meter as well as a portable computing device, such as a mobile phone. Given the close proximity of these two devices, the portable computing device can serve as a data collector for the glucose measures taken by the glucose meter. Improved techniques are set forth for transferring glucose measures automatically and seamlessly to the patient's portable computing device.

In one aspect of this disclosure, a method is provided for displaying status during a wireless transmission of a glucose measure from a handheld glucose meter to a diabetes management application residing on a portable computing device. The method includes: determining a blood glucose measure from a test strip inserted into a port of the glucose meter; displaying the blood glucose measure on a result screen of the glucose meter, the display of the blood glucose measure being performed in response to the determination of the blood glucose measure; transferring the blood glucose measure via a wireless data link to the diabetes management application; and displaying an interface on the display of the glucose meter concurrently with the transfer of the blood glucose measure to the diabetes management application, where the interface provides an indication of the data transfer, a numeric value for the blood glucose measure and an identifier for the portable computing device.

In some embodiments, the blood glucose measure is transferred automatically in response to the determination of the blood glucose measure and without user intervention.

In other embodiments, the blood glucose measure is transferred in response to the user navigating away from the result screen. For example, the user may navigate from the result screen to a comment selection screen, the comment selection screen presenting a listing of comments for selection. Upon receiving a selection of a comment from the listing of comments, the user is navigated from the comment selection screen back to the result screen. In this example, the transfer of the blood glucose measure is deferred until the comment has been associated with the blood glucose measure.

During pairing of the glucose meter with the portable computing device, the user may be prompted to input a name for the portable computing device, such that the name of the portable computing device may serve as the identifier for the portable computing device on the interface.

In another aspect of this disclosure, a handheld glucose meter is presented with an improved user interface for displaying status during transmission of a blood glucose measure. The glucose meter includes: a port configured to receive a test strip; having a reaction site for receiving a sample of blood from a patient; a glucose measurement module cooperatively operable with a test strip inserted in the port to measure glucose in a sample of blood residing on the test strip; and a wireless transceiver that operates to communicate the glucose measure received from the glucose measurement module automatically via a wireless data link to a diabetes management application residing on a portable computing device. The glucose meter further includes a user interface module in data communication with the glucose measurement module and the wireless transceiver. The user interface module operates to display the glucose measure on a result screen of the glucose meter immediately following the determination of the glucose measure by the glucose measurement module. The user interface module also presents an interface on the display of the glucose meter concurrently with the transfer of the glucose measure to the diabetes management application, where the interface provides an indication of the data transfer, a numeric value for the glucose measure and an identifier for the portable computing device.

This section provides a general summary of the disclosure, and is not a comprehensive disclosure of its full scope or all of its features. Further areas of applicability will become apparent from the description provided herein. The description and specific examples in this summary are intended for purposes of illustration only and are not intended to limit the scope of the present disclosure.

DRAWINGS

Figure 1:
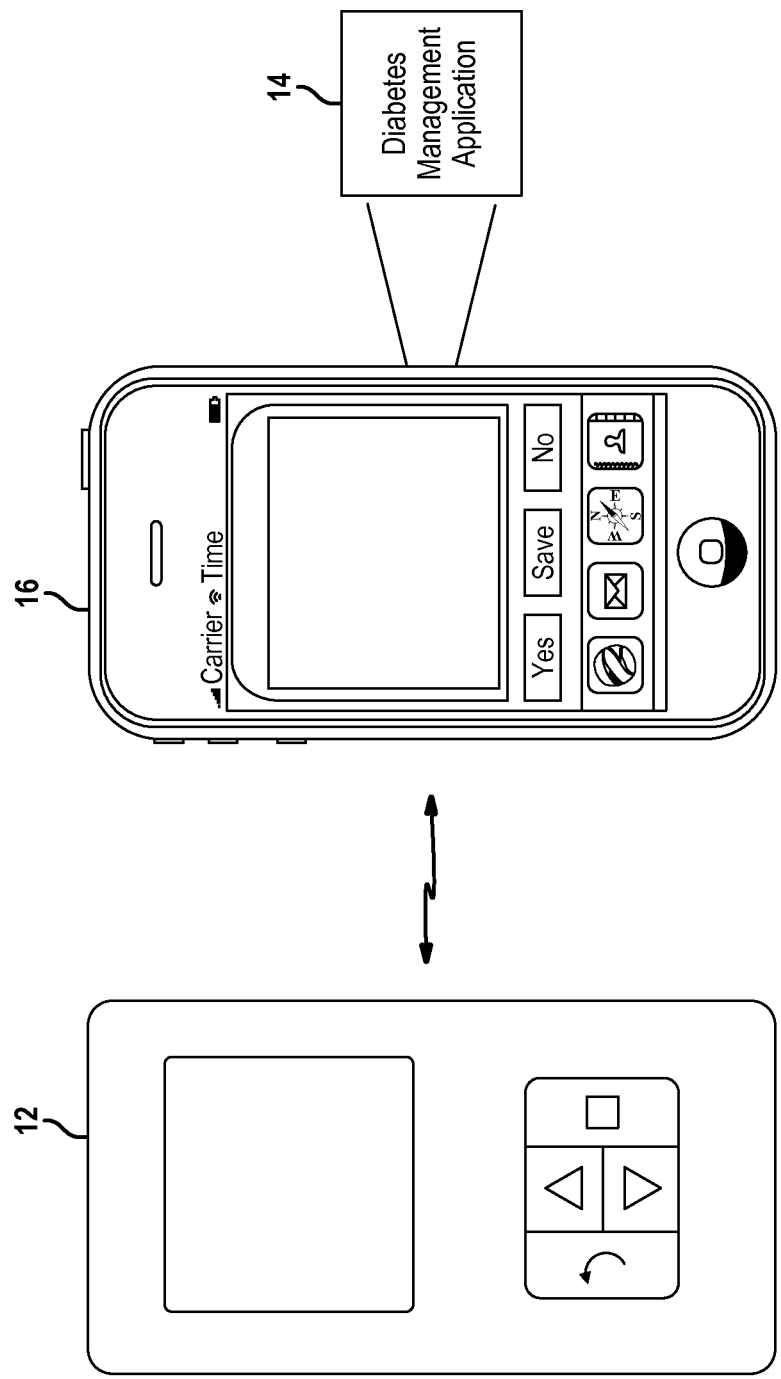
FIG. 1 is a diagram depicting a handheld glucose meter in data communication with a diabetes management application residing on a mobile phone.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

FIG. 1 depicts an exemplary handheld glucose meter 12 in data communication via a wireless data link with a diabetes management application 14. The glucose meter 12 is configured to receive a sample of blood from a patient and determine a blood glucose measure for the patient from the blood sample. One or more blood glucose measures may in turn be transmitted over the wireless data link to the diabetes management application 14 for further processing. In an exemplary embodiment, the diabetes management application 14 resides on a mobile phone 16. In other embodiments, the diabetes management application may be native to a remote server with its user interface presented on the mobile phone 16. In some embodiments, data is transferred to and from the glucose meter 12 using the Bluetooth wireless technology standard (e.g., low energy feature of Bluetooth 4.0) although other types of communication transports are contemplated by this disclosure.

Figure 2:
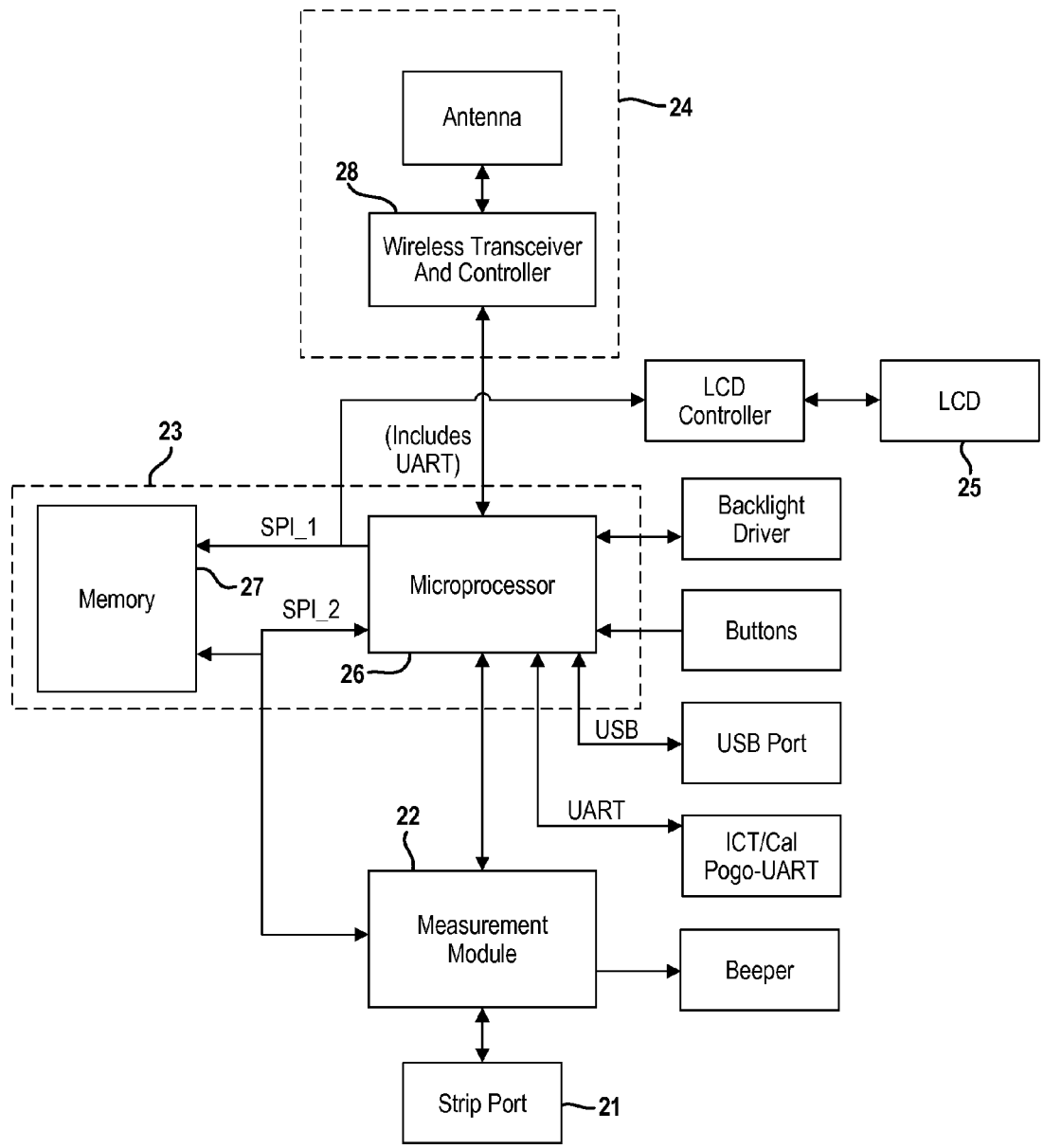
FIG. 2 is a block diagram of an exemplary hardware arrangement for the glucose meter.

FIG. 2 depicts an exemplary hardware arrangement for the glucose meter 12. The glucose meter 12 is comprised generally of a measurement module 22, a processing subsystem 23 and a communication subsystem 24. Each of these components is further described below. While the primary components are discussed herein, it is understood that other components (e.g., batteries) may be needed for the overall operational of the meter.

The measurement module 22 cooperatively interacts with a test strip inserted into a strip port 21 to determine a glucose measure from the sample of blood on the test strip. The measurement module 22 may include a code key that includes calibration information for the test strips being read by the meter. As used herein, the term module may refer to, be part of, or include an application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above. The term module may further include memory that stores code executed by the processor, where code, as used above, may include software, firmware, and/or microcode, and may refer to programs, routines, functions, classes, and/or objects.

The processing subsystem 23 is configured to receive the glucose measures from the measurement module 22 which may in turn be stored by the processing subsystem 23. Glucose measures may also be displayed by the processing subsystem 23 on a display 25. The user can interact with the meter using various user interface components, such as buttons, switches, a speaker, a microphone, USB port, etc. Each of these components is interfaced with the processing subsystem 23. In an exemplary embodiment, the processing subsystem 23 includes a microprocessor 26 and one or more volatile and/or non-volatile memories 27 although other implementations are envisioned for the processing subsystem.

The processing subsystem 23 is also interfaced with the communication subsystem 24. In an exemplary embodiment, the communication module includes a wireless transceiver 28. The wireless transceiver operates to communicate the glucose measures and other data wirelessly via a data link to a remote device physically separated from the meter. The communication subsystem can also include an antenna, microcontroller, voltage and power control circuits and a flash memory device. Although a few primary components of the meter 12 are discussed herein, it is readily understood that other components (e.g., power source) may be needed to implement the meter.

Figure 3:
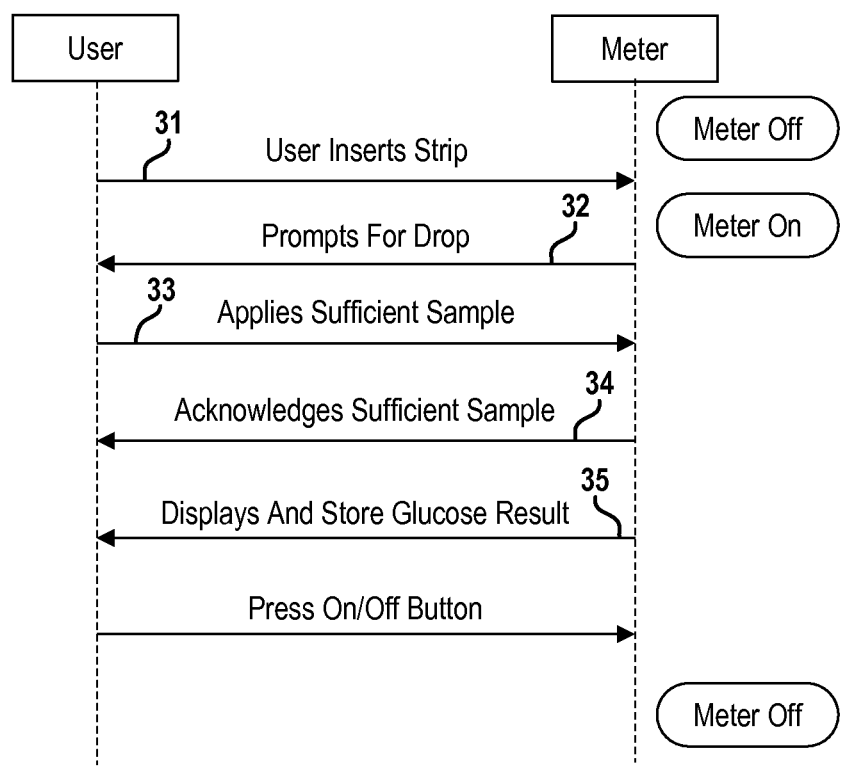
FIG. 3 is a sequence diagram illustrating an exemplary sequence for taking a blood glucose measure using the glucose meter.

FIG. 3 depicts an exemplary sequence for taking a blood glucose measure using the blood glucose meter 12. The user may insert a test strip at 31 into a port of the glucose meter. Insertion of the test strip prompts the glucose meter to power on. The user may alternatively power on the glucose meter using an on/off button. In this case, the glucose meter will prompt the user to insert a test strip. The user may also power on the glucose meter without having inserted a test strip into the meter. In any of these cases, the glucose meter may perform a quality check on the test strip inserted into the meter. Once the quality check has been completed, the meter is ready to perform a test.

To begin a test, the user is prompted at 32 for a sample of blood. In response to the prompt, the user provides a blood sample at 33 using the test strip, where the test strip includes a reaction site that receives the blood sample from the patient. Upon receipt of the blood sample, the glucose meter will proceed to analyze the blood sample in a manner readily known in the art. Before doing so, the glucose meter may acknowledge the sufficiency of the blood as indicated at 34.

During the analysis, a blood glucose measure is obtained from the blood sample. The blood glucose measure will be displayed to the user and stored on the glucose meter as indicated at 35. Stored glucose measures may be uploaded subsequently from the glucose meter in a batch manner to a physician's computer.

Figure 4:
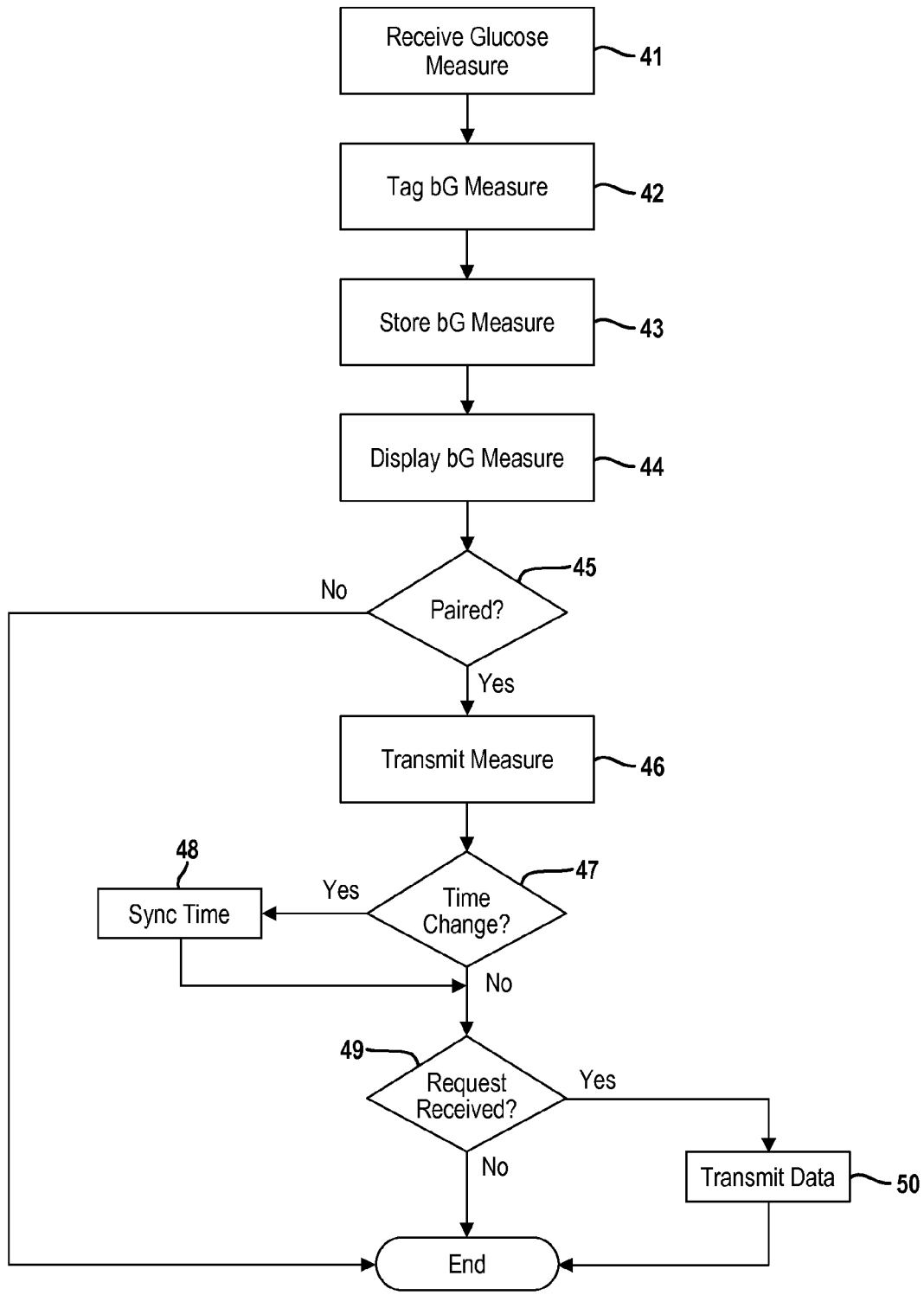
FIG. 4 is a flowchart illustrating an exemplary technique for transmitting blood glucose measures individually from the glucose meter.

Rather than sending blood glucose measures in a batch manner, the glucose meter may be configured to transmit blood glucose measures individually as shown in FIG. 4. The blood glucose measures may be transmitted, for example to a mobile phone or some other portable computing device carried by the user. Because the mobile phone is typically in close proximity to the user, it may be used as a data collector for the patient's blood glucose measures. A diabetes management application 14 residing on the mobile phone 16 can then be used for data analysis as well as other sophisticated diabetes management functions. Consequently, the processing power and memory available on the glucose meter can be streamlined, thereby reducing the cost of the glucose meter 12.

Upon determining a blood glucose measure, the blood glucose measure is first tagged at 42 with identifying information. Identifying information may include but is not limited to a name of the patient to which the measure pertains to, a timestamp for when the measure was taken, a serial number for the meter and other information pertaining to the test strip. Of note, each blood glucose measure is also tagged with a unique sequence number assigned by the glucose meter. In one embodiment, a counter is incremented each time a glucose measure is taken and the value of the counter is assigned to the blood glucose measure. The sequence number may be used to retrieve missing data from the glucose meter as is further described below. Once tagged, the blood glucose measure is stored at 43 in a memory of the glucose meter and displayed to the user at 44 on a display of the glucose meter.

Next, the glucose meter determines at 45 whether it is paired via a wireless data link with another device, such as mobile phone 16. The current blood glucose measure is transmitted at 46 to the mobile phone when the glucose meter is paired to the mobile phone. In one embodiment, the blood glucose measure is transmitted automatically and without user intervention. In another embodiment, the blood glucose measure is transmitted automatically in response to the user navigating away from the measurement result screen as will be further described below. It is envisioned that the mobile phone and/or the diabetes management application is authenticated with the glucose meter during the pairing process.

In addition to transmitting the blood glucose measure, the glucose meter can synchronize its time with the mobile phone. During initial setup or thereafter, the glucose meter may be configured by the user, using either the blood glucose meter or the mobile phone, to synchronize its clock with the mobile phone. By enabling this time synchronization feature, the user is designating the mobile phone as the master device. Current time on the mobile phone is transmitted to the glucose meter during each data exchange. Because a user is interacting frequently with their mobile phone, the time reported by the mobile phone is likely to be accurate. The glucose meter will compare the current time on the mobile phone to the current time maintained by the glucose meter as indicated at 47. If the time synchronization feature has been enabled by the user and the difference between the two clocks exceeds a variance (e.g., 2 minutes), the glucose meter will set its clock to the current time of the mobile phone as indicated at 48. Conversely, the glucose meter may retain its current time if time synchronization feature has not been enabled or the difference between the two clocks is less than the variance threshold. In an alternative embodiment, the glucose meter will set its clock to the current time of the mobile phone if the difference between the two clocks is less than the variance threshold and the time synchronization feature is enabled. It is envisioned that other parameters, such as date/time format, target glucose ranges, hypo waning levels, etc., can also be synchronized between the two devices.

During each data exchange, the glucose meter may also receive a request for missing glucose measures at 49 from the diabetes management application. In one embodiment, the request identifies any missing glucose measures by its sequence number as will be further described below. In response to receiving a request, the glucose meter will transmit the missing glucose measures at 50 to the diabetes management application. It is to be understood that only the relevant steps are discussed in relation to FIG. 4 but that other software-implemented instructions may be needed to transmit data from the glucose meter. In an exemplary embodiment, the method described above is implemented by a user interface module residing on the glucose meter.

Figure 5:
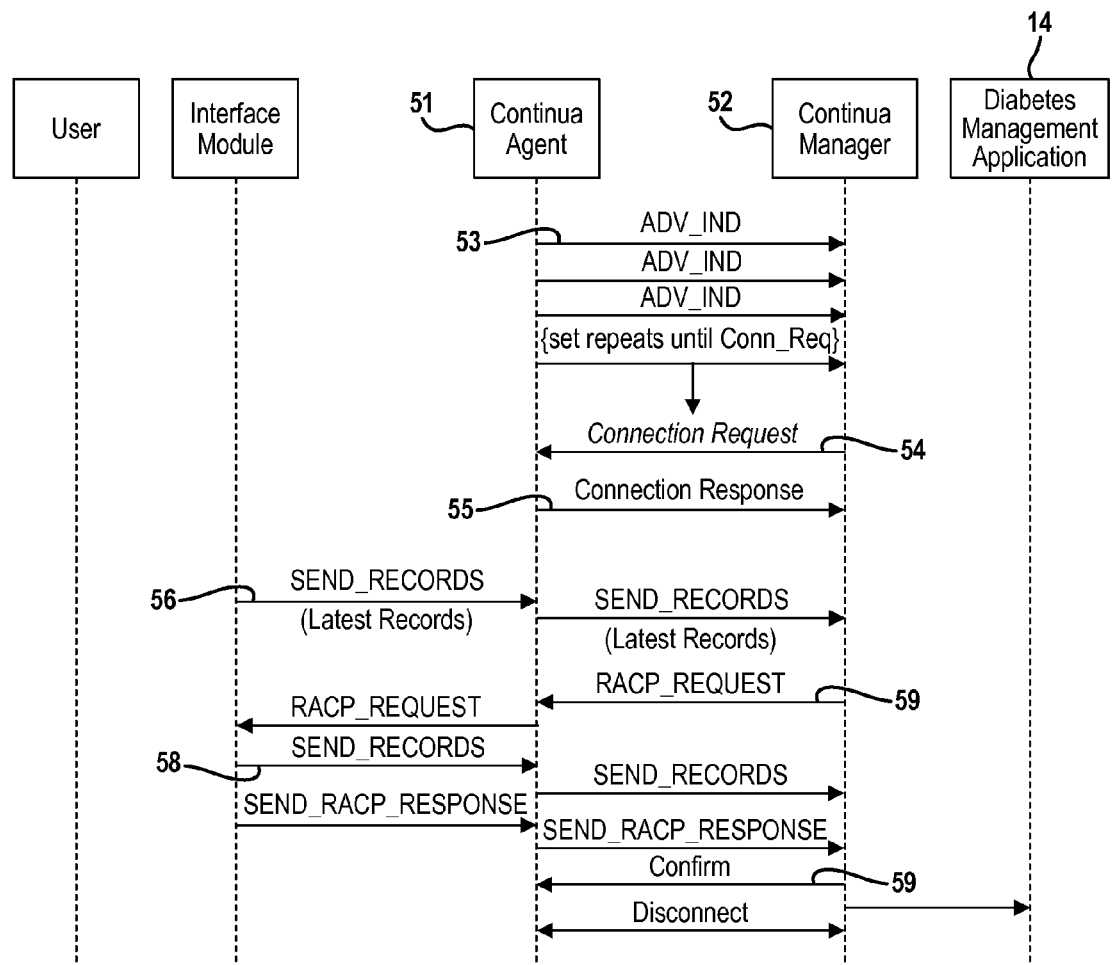
FIG. 5 is a sequence diagram depicting an exemplary data transmission between the glucose meter and the mobile phone.

FIG. 5 further illustrates an exemplary embodiment for implementing data transmission between the glucose meter 12 and the mobile phone 16. In this exemplary embodiment, data transmission occurs in accordance with IEEE standard 11073, the Bluetooth specification, and the Continua BLE specification. The communication model employs the concept of "managers" and "agents". Agents are typically smaller personal health devices that lack processing power; whereas, managers tend to be more powerful computing devices such as a mobile phone or desktop computer. Each device performs certain roles in accordance with its designation. To implement its role, each device is configured with an interface component which implements the functions associated with its designated role. In this case, the glucose meter is configured with an agent component 51 and the mobile phone is configured with a manager component 52. While reference is made to a particular communication protocol, it is readily understood that concepts disclosed herein extend more broadly to other communication protocols.

To establish a communication session, the agent 51 initiates a connection with the manager 52 as indicated at 53. In response thereto, the manager 52 sends a connection request at 54 to the agent 51. In one embodiment, the connection request may include the current time maintained by the mobile phone. The current time may be used to synchronize the time on the glucose meter as described above. The agent 51 in turn responds to the connection request as indicated at 55, thereby establishing a connection between the agent and the manager.

Once a connection has been established, the current glucose measure can be sent from an interface module to the agent 51 which in turn transmits the glucose measure to the manager 52 as indicated at 56, where the interface module is implemented by the processing subsystem 23. The glucose measures can then be passed along to the diabetes management application 14 for subsequent processing as described below.

In addition, the manager 52 may send a request at 57 for any missing glucose measures to the glucose meter. The request is relayed by the agent 51 to the interface module which in turn handles the request. That is, the interface module retrieves any missing glucose measures identified in the request and sends those glucose measures back to the agent 51 as indicated at 58. The agent 51 then sends the missing glucose measures to the manager 52. The manager 52 may confirm receipt of the missing glucose measures at 59 and then proceed to terminate the connection with the agent.

In some instances, the data transmission from the meter to the mobile phone may be unsuccessful. The meter may be configured to periodically attempt to resend the glucose measure to the mobile phone. If the user attempts to power down the meter before a successful data transmission, the meter may continue to periodically attempt to resend the glucose measure to the mobile phone. The next time the meter is powered on, the user may be presented a message that the glucose measure was successfully transmitted to the mobile phone.

Figure 6:
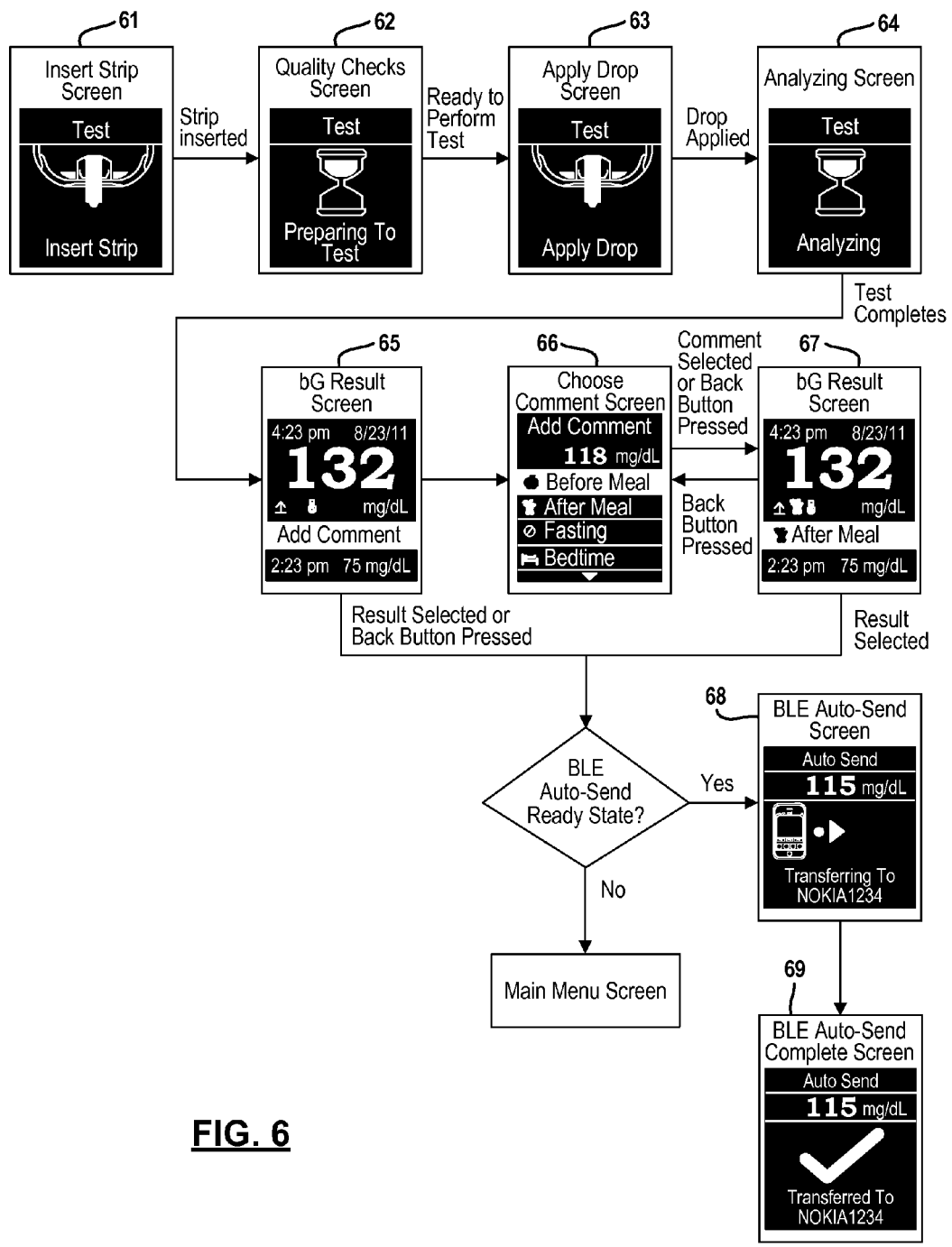
FIG. 6 depicts example screens displayed on the glucose meter during a testing scenario.

FIG. 6 illustrates example screens displayed on the glucose meter during a testing scenario. From a main menu screen, the user may elect to perform a glucose test. The insert strip screen is displayed as shown at 61 when the user selects the perform test item on the main menu and a test strip is not inserted into the meter. Once a test strip has been inserted, the quality check screen appears as shown at 62 and is displayed while a quality check is performed by the meter. The quality check screen may also appear when the user selects the perform test item on the main menu and a test strip is present in the meter. Once the quality check has been completed, the meter is ready to perform a test.

To begin a test, the user is prompted to apply a blood sample as shown at 63. In response to the prompt, the user provides a blood sample using the test strip, where the test strip includes a reaction site that receives the blood sample from the patient. Upon receipt of the blood sample, the glucose meter will proceed to analyze the blood sample in a manner readily known in the art. The analyzing screen appears as shown at 64 and is displayed while the test is being performed by the meter.

Once the test completes, a blood glucose measure is displayed on the bG result screen as shown at 65. A numeric value for the blood glucose measure is displayed along with other information pertaining to the measure. Upon seeing the glucose measure, the user may elect to navigate away from the result screen, for example by depressing the <back> button on the meter. In this case, the user will return to the main menu screen and the result will be transmitted.

Alternatively, upon seeing the glucose measure, the user may elect to enter a comment pertaining to the glucose measure. To do so, the user may use the <up> or <down> buttons to select the add comment function on the screen. The choose comment screen will appear as shown at 66. In the exemplary embodiment, the user may select from a listing of comments which include before meal, after meal, fasting and bedtime. After the user selects a comment from the list, the result screen appears as shown at 67. It is noted that the selected comment is displayed along with the glucose measure on the result screen. After reviewing the annotated result, the user may elect to navigate away from the result screen.

In response to navigating way from the result screen, the glucose meter will try transmitting the glucose measure, including any comment, automatically to a paired device. The glucose meter will determine if it is paired with a device having an authenticated diabetes management application and, if so, initiate transmission of the current glucose measure to the paired device in the manner discussed above.

During data transmission, the auto-send screen is displayed as shown at 68. The auto-send screen will include an indicator that a transfer is occurring, such as a blinking arrow extending away from a meter icon. The auto-send screen will also include a value for the glucose measure being sent (i.e., 115 mg/dL) as well as an identifier for the device receiving the data transmission (i.e., NOKIA1234). Depending on the value of the glucose measure, the user may need to take some action immediately, such as administer insulin or contact a physician. Therefore, it is important that the glucose measure remain available to the user during the data transmission. Because the glucose meter may pair with many different devices, it is also important that the user be advised as to which device the glucose measure is being sent to, thereby avoiding transmission to an erroneous device. For example, only one of the available devices may be configured with an insulin recommendation function. In one embodiment, the identifier may be a serial number for the portable computing device or some other type of identifier, for example obtained from the portable computing device during the pairing process. Rather than display a serial number for the portable computing device, the glucose meter may be configured to display a more intuitive identifier for the portable computing device, such as Tim's phone. In one embodiment, the glucose meter can prompt a user to input a name for the portable computing device, for example during or shortly after pairing with the portable computing device. The name provided by the user is stored in memory and can be displayed on the auto-send screen as described above. Upon completion of the data transfer, the auto-send complete screen appears as shown at 69.

Figure 7:
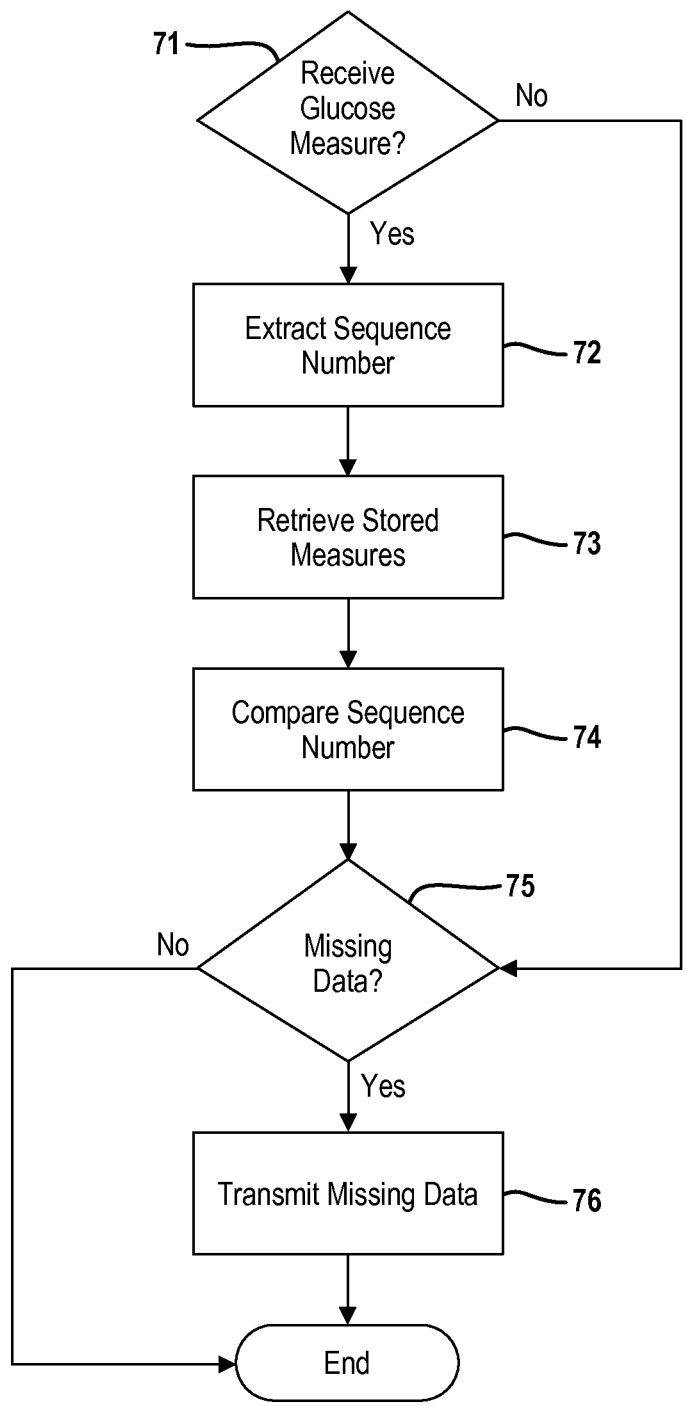
FIG. 7 is a flowchart illustrating an exemplary technique for processing glucose measures received by the diabetes management application.

FIG. 7 depicts an exemplary method for processing glucose measures received by the diabetes management application 14 residing on the mobile phone. In the exemplary embodiment, glucose measures are transmitted individually to the diabetes management application 14 as described in relation to FIG. 4. It is envisioned that other techniques for transmitting the glucose measure to the diabetes management application 14 are contemplated by this disclosure.

Upon receiving a glucose measure, a sequence number associated with the glucose measure is first determined by the diabetes management application. A unique sequence number is assigned by the glucose meter to each glucose measure as described above. Thus, the sequence number associated with the glucose measure can be extracted at 72 from the data packet or message received from the glucose meter. In some embodiments, a series of glucose measures previously received from the glucose meter, along with their associated sequence numbers, may be stored in a memory device and thus accessible to the diabetes management application. In other embodiments, only the most recently received glucose measure and its sequence number is stored by the diabetes management application. In either case, the stored glucose measure(s) along with associated sequence number(s) are retrieved from memory.

A comparison is made at 74 between the sequence number extracted from the present glucose measure and the sequence numbers of the stored glucose measures. A request for missing glucose measures is transmitted by the diabetes management application to the glucose meter when an omission in the sequence is detected. For example, a request for missing glucose measures is transmitted at 76 when the extracted sequence number is 74 and the highest stored sequence number is either 71 or 72. Conversely, a request is not transmitted when the extracted sequence number is 74 and the highest stored sequence number is 73. Because this comparison is made for each glucose measure received by the diabetes management application, a comparison of the extracted sequence number only needs to be made to the highest stored sequence number. In other embodiments, the diabetes management application may analyze the series of glucose measure for omitted measures and send a request for each glucose measure missing from the series of glucose measures. The request for missing glucose measures can be transmitted in accordance with the protocol described in relation to FIG. 5.

Even when a glucose measure is not received, the diabetes management application can check for omitted glucose measures as indicated at 71. As noted above, the diabetes management application can analyze the series of glucose measures for omitted measures and send a request at 76 for each glucose measure missing from the series of glucose measures. It is to be understood that only the relevant steps are discussed in relation to FIG. 7 but that other software-implemented instructions may be performed by the diabetes management application.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are non-volatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

What is claimed is:

1. A method for displaying status during a wireless transmission of a glucose measure from a handheld glucose meter to a diabetes management application residing on a portable computing device, comprising:
   determining, by the glucose meter, a blood glucose measure from a test strip inserted into a port of the glucose meter, the test strip having a reaction site for receiving a sample of blood from a patient;
   displaying, by the glucose meter, the blood glucose measure on a result screen of the glucose meter, the display of the blood glucose measure being performed in response to the determination of the blood glucose measure;
   navigating, in response to an input command, from the result screen to a comment selection screen, the comment selection screen presenting a listing of comments for selection;
   receiving a selection of a comment from the listing of comments;
   navigating from the comment selection screen to the result screen; and
   transferring the blood glucose measure via a wireless data link to the diabetes management application in response to navigating away from the result screen after returning to the result screen once a comment from the selection screen has been chosen; and
   displaying, by the glucose meter, an interface on a display of the glucose meter concurrently with the transfer of the blood glucose measure to the diabetes management application, where the interface provides an indication of a data transfer, a numeric value for the blood glucose measure and an identifier for the portable computing device.

2. The method of claim 1 further comprises transferring the blood glucose measure automatically in response to the determination of the blood glucose measure and without user intervention.

3. The method of claim 1 further comprises transferring the blood glucose measure in response to navigating away from the result screen.

4. The method of claim 1 further comprises
   pairing, by the glucose meter, with the portable computing device to thereby establish the wireless data link;
   prompting, by the glucose meter, input of a name for the portable computing device; and
   receiving, by the glucose meter, a name for the portable computing device in response to the prompt, where the name of the portable computing device serves as the identifier for the portable computing device on the interface.

5. The method of claim 1 further comprises:
   receiving, by the glucose meter, current time from the portable computing device during the transmission of the blood glucose measure;
   synchronizing, by the glucose meter, a clock maintained by the glucose meter with the current time received from the portable computing device when a difference between time of the clock and the current time exceeds a variance threshold.

6. The method of claim 1 further comprises:
   receiving, by the glucose meter, a request for a missing glucose measure, where the request identifies the missing glucose measure by a sequence number assigned by the glucose meter; and
   transmitting, by the glucose meter, the missing glucose measure via the wireless data link to the diabetes management application, where the transmission occurs automatically in response to receiving the request.

7. The method of claim 1 further comprises transferring the blood glucose measure in accordance with a low energy feature of Bluetooth wireless technology standard.

8. A handheld glucose meter having an improved user interface for displaying status during transmission of a blood glucose measure, comprising:
   a port configured to receive a test strip having a reaction site for receiving a sample of blood from a patient;
   a glucose measurement module cooperatively operable with a test strip inserted in the port to measure glucose in a sample of blood residing on the test strip;
   a wireless transceiver in data communication with the glucose measurement module and operable to communicate the glucose measure received from the glucose measurement module automatically via a wireless data link to a diabetes management application residing on a portable computing device and being physically separated from the glucose meter; and
   a user interface module in data communication with the glucose measurement module and the wireless transceiver, the user interface module operates to display the glucose measure on a result screen of the glucose meter immediately following the determination of the glucose measure by the glucose measurement module and operates to display an interface on a display of the glucose meter concurrently with the transfer of the glucose measure to the diabetes management application, where the interface provides an indication of a data transfer, a numeric value for the glucose measure and an identifier for the portable computing device, wherein the user interface module navigates, in response to an input command, from the result screen to a comment selection screen, the comment selection screen presents a listing of comments for selection; and, in response to receiving a comment, navigates from the comment selection screen back to the result screen; wherein the wireless transceiver transfers the blood glucose measure and the comment in response to navigating away from the result screen after returning to the result screen once a comment from the selection screen has been chosen.

9. The handheld glucose meter of claim 8 wherein the wireless transceiver transfers the glucose measure automatically in response to the determination of the glucose measure by the glucose measurement module and without user intervention.

10. The handheld glucose meter of claim 8 wherein the wireless transceiver transfers the glucose measure in response to navigating away from the result screen.

11. The handheld glucose meter of claim 8 wherein the user interface module prompts input of a name for the portable computing device during pairing of the glucose meter with the portable computing device and receives a name for the portable computing device in response to the prompt, where the received name is displayed as the identifier of the portable computing device on the interface.

12. The handheld glucose meter of claim 8 wherein the user interface module is configured to receive current time from the portable computing device during transmission of the blood glucose measure and operates to synchronize a clock maintained by the glucose meter with the current time received from the portable computing device when a difference between time of the clock and the current time exceeds a variance threshold.

13. The handheld glucose meter of claim 8 wherein the user interface module is configured to receive a request for a missing glucose measure from the portable computing device and interacts with the wireless transceiver to transmit the missing glucose measure via the wireless data link to the diabetes management application, where the request identifies the missing glucose measure by a sequence number assigned by the glucose meter and the transmission occurs automatically in response to receiving the request.

* * * * *